United States Patent [19]

Adams et al.

[11] Patent Number: 4,770,801

[45] Date of Patent: * Sep. 13, 1988

[54] COUPLED PHOSPHORUS-CONTAINING AMIDES, PRECURSORS THEREOF AND LUBRICANT COMPOSITIONS CONTAINING SAME

[75] Inventors: Paul E. Adams, Willoughby; Carmen V. Luciani, Wickliffe, both of Ohio

[73] Assignee: The Lubrizol Corporation, Wickliffe, Ohio

[ * ] Notice: The portion of the term of this patent subsequent to Jun. 2, 2004 has been disclaimed.

[21] Appl. No.: 35,550

[22] Filed: Apr. 7, 1987

Related U.S. Application Data

[60] Division of Ser. No. 853,485, Apr. 18, 1986, Pat. No. 4,670,169, which is a continuation-in-part of Ser. No. 730,877, May 3, 1985.

[51] Int. Cl.$^4$ .......................................... C10M 133/16
[52] U.S. Cl. ...................................... 252/46.7; 252/49.9
[58] Field of Search ................ 558/159, 170; 252/46.7

[56] References Cited

U.S. PATENT DOCUMENTS

| | | | |
|---|---|---|---|
| 2,901,481 | 8/1959 | Fusco et al. | 558/159 |
| 3,238,202 | 3/1966 | Peri et al. | 558/170 |
| 3,265,773 | 8/1966 | Loaco et al. | 558/170 |
| 3,845,171 | 10/1974 | Beriger | 558/170 |
| 3,933,945 | 1/1976 | Beriger | 558/170 |
| 3,991,140 | 11/1976 | Beriger | 558/170 |
| 4,032,461 | 6/1977 | Hoke | 252/46.7 |
| 4,162,279 | 7/1979 | Walsh et al. | 558/170 |
| 4,177,300 | 12/1979 | Walsh et al. | 558/170 |
| 4,208,357 | 6/1980 | Hoke | 260/978 |
| 4,282,171 | 8/1981 | Hoke | 260/928 |
| 4,333,841 | 6/1982 | Schmidt et al. | 558/170 |
| 4,418,021 | 11/1983 | Patel | 558/170 |
| 4,453,965 | 6/1984 | Patel | 558/170 |
| 4,579,691 | 4/1986 | Maier et al. | 558/170 |
| 4,670,169 | 6/1987 | Adams et al. | 252/46.7 |

OTHER PUBLICATIONS

German Patent Wolf et al., Deutsche Lebensmittel-Rundschau, vol. 64 (6) pp. 171–177, 1968.

Primary Examiner—William R. Dixon, Jr.
Assistant Examiner—Ellen McAvoy
Attorney, Agent, or Firm—Karl Bozicevic; Denis A. Polyn; William C. Tritt

[57] ABSTRACT

A load-carrying agent and a lubricating composition containing such an agent is disclosed. The agent is preferably comprised of a statistical mixture of a plurality of different coupled phosphorus-containing amide compounds having the formula

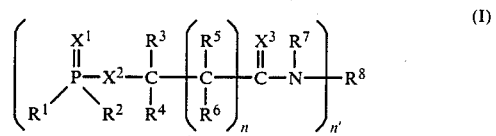

wherein $X^1$, $X^2$ and $X^3$, independently, is O or S; wherein $R^1$ and $R^2$, independently, is a hydrocarbyl, a hydrocarbyl-based oxy, the hydrocarbyl portion of which contains 6 to 22 carbon atoms, or a hydrocarbyl-based thio having from 4 to about 34 carbon atoms; wherein $R^3$, $R^4$, $R^5$ and $R^6$, independently, is hydrogen, or an alkyl having from 1 to about 22 carbon atoms, a cycloalkyl having from about 4 to about 22 carbon atoms, or an aromatic, an alkyl-substituted aromatic or an aromatic-substituted alkyl having from 6 to about 34 carbon atoms; wherein n is 0 or 1; wherein n' is 1, 2 or 3; wherein $R^7$ is hydrogen or an alkyl having from 1 to 22 carbon atoms; and wherein when n' is 1, $R^8$ is selected from the group consisting of H, —ROH, —ROR, —RSR and

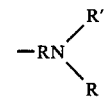

and when n' is 2, $R^8$ is selected from the group consisting of

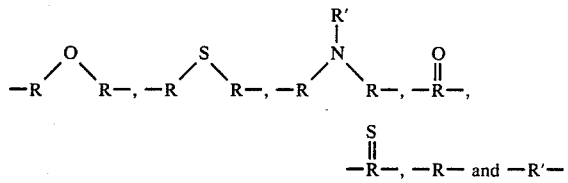

when n' is 3, $R^8$ is

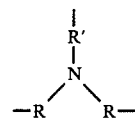

wherein R is independently hydrogen or an alkyl moiety, alkylene or alkylidene containing 1 to 12 carbon atoms and R' is hydrogen or an alkyl moiety, alkylene, alkylidene or carboxyl containing 1 to 60 carbon atoms.

9 Claims, No Drawings

COUPLED PHOSPHORUS-CONTAINING AMIDES, PRECURSORS THEREOF AND LUBRICANT COMPOSITIONS CONTAINING SAME

CROSS-REFERENCES

This is a divisional of co-pending application Ser. No. 853,485 filed on Apr. 18, 1986, now U.S. Pat. No. 4,670,169, which is a continuation-in-part application of co-pending application Ser. No. 730,877, filed on May 3, 1985, which is incorporated herein in its entirety. We claim priority under 35 USC §120 with respect to any and all disclosure made in said earlier filed U.S. application Ser. No. 730,877.

FIELD OF THE INVENTION

The present invention relates to coupled phosphorus-containing amides, their precursors, lubricant concentrates, and lubricants containing same which can be employed in the lubrication of internal combustion engines, hydraulic equipment, and the like. The coupled amides can be prepared, for example, by the reaction of acids such as dialkyl and/or diaryl phosphorodithioic acids reacted with unsaturated hydrocarbyl acrylamides and subsequently coupled by a coupling reaction carried out in the presence of formaldehyde and/or paraformaldehyde.

BACKGROUND OF THE INVENTION

German Pat. No. 819,998 relates to a method of producing esters of phosphoric acid or thiophosphoric acid containing a carboxylic acid amide group.

An article by Wolf and Heidenreich, Deutsche Lebensmittel Rundschau, Vol. 64, No. 6, pages 171–177 (1968) relates to the synthesis of organic phosphorus compounds with insecticidal and acaricidal activity such as N,N'-methylenebis (O,O-dialkylphosphorylmercaptoacylamine) wherein the alkyl portion of the dialkyl phosphoryl groups contain 1–4 carbon atoms and the amides may be coupled via a methylene coupler.

U.S. Pat. No. 4,032,461 to Hoke relates to phosphorus and sulfur-containing amides and thioamides as lubricating oil additives and lubricating oil compositions containing the same.

U.S. Pat. No. 4,208,357 to Hoke relates to a process for preparing phosphorus and sulfur-containing amides and thioamides.

U.S. Pat. No. 4,282,171 to Hoke also relates to phosphorus and sulfur-containing amides and thioamides.

SUMMARY OF THE INVENTION

Accordingly, it is an aspect of the present invention to provide coupled phosphorus-containing amide and/or phosphorus-sulfur containing compounds (hereinafter referred to as simply phosphorus-containing amide compounds), the compounds being coupled via an alkylene, ether, thioether, amino, or carboxyl linking groups.

It is a further aspect of the present invention to provide a mixture, of coupled phosphorus-containing amide compounds and other functional derivatives of phosphorus-containing amides in a lubricating composition wherein the coupling group is represented by one or more of the following structural formula

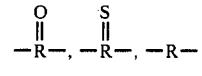

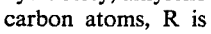

wherein R is independently hydrogen or an alkyl containing 1 to 8 carbon atoms and R' is independently hydrogen or an alkyl or carboxyl alkyl moiety, alkylene or alkylidene containing 1 to 60 carbon atoms, R is preferably methyl and R' is preferably an alkyl moiety, alkylene or alkylidene containing 1 to 28 carbon atoms. Three phosphorus-containing amide compounds can be coupled when the coupler is

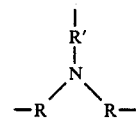

It is a further aspect of the present invention to provide an effective load-carrying agent in the form of a mixture of such coupled phosphorus-containing amide compounds and their precursors and other functional derivatives of phosphorus-containing amides in minor amounts with other additives in a major amount of a lubricating oil or other functional fluids.

These and other aspects of the present invention will become apparent to those skilled in the art from the attached specification which fully describes the present invention.

A particularly preferred embodiment of the present invention is a lubricating composition comprising a major portion of a lubricating oil and a minor portion of a load-carrying agent in the form of a mixture of compounds which are encompassed by the general formula

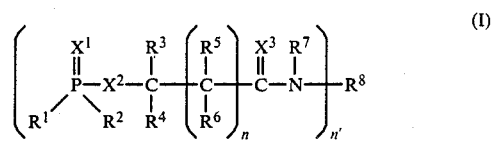

(I)

wherein $X^1$, $X^2$ and $X^3$, independently, is O or S;

wherein $R^1$ and $R^2$, independently, is a hydrocarbyl, a hydrocarbyl-based oxy, the hydrocarbyl portion of which is an alkyl-containing 6 to 22 carbon atoms or a hydrocarbyl-based thio, having from 4 to about 34 carbon atoms;

wherein $R^3$, $R^4$, $R^5$ and $R^6$, independently, is hydrogen, or an alkyl having from 1 to about 22 carbon atoms, a cycloalkyl having from 4 to about 22 carbon atoms, or an aromatic, an alkyl-substituted aromatic or an aromatic-substituted alkyl having from 6 to about 34 carbon atoms;

wherein n is 0 or 1;

wherein n' is 1, 2 or 3;

wherein $R^7$ is hydrogen or an alkyl having from 1 to 22 carbon atoms; and wherein when n' is 1, $R^8$ is hydrogen, —ROH, —ROR, —RSR,.

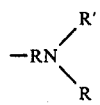

and when n' is 2, $R^8$ is

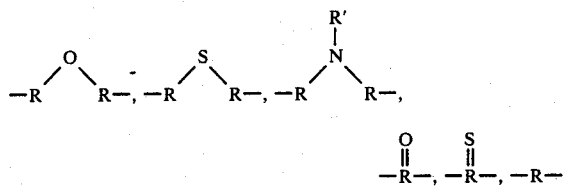

when n' is 3, $R^8$ is

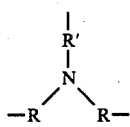

wherein R is independently hydrogen, an alkyl moiety, alkylene or alkylidene of 1 to 12 carbons and R' is hydrogen, an alkyl or carboxy alkyl moiety, alkylene or alkylidene containing 1 to 60 carbons, R is preferably methylene and R' is preferably an alkyl or carboxy alkyl, alkylene, alkylidene containing 1 to 28 carbons.

When n' is 1 or 2, the R' and/or R can be a coupling group as defined above, hydrogen or an alkyl or carboxy alkyl moiety corresponding to the above referred to linking group. With respect to when any $R^8$ is a coupling group, the R and R' cannot be hydrogen and must be a coupler such as an alkylene or alkylidene to link together phosphorus-containing amide.

DETAILED DESCRIPTION OF THE PREFERRED EMBODIMENTS

The coupled amide compounds of Formula I (i.e., when n' is 2 or 3) are obtained by the coupling reaction of phosphorus-containing amides. While the uncoupled phosphorus-containing amides are intermediates they are themselves useful compounds, e.g., load-carrying agents in a lubricant oil and can be reacted to include an R8 functional group when n' is 1. Such uncoupled phosphorus-containing amides are likely to be present together with coupled phosphorus-containing compounds of Formula I as used as load-carrying agents in a lubricating oil. Accordingly, load-carrying agents of the present invention may be, and preferably are, comprised of mixtures of compounds including: (1) a mixture of different uncoupled phosphorus-containing amides (n' is 1); (2) a mixture of coupled phosphorus-containing amides (n' is 2); and (3) a mixture of coupled phosphorus-containing amides when n' is 3; which includes coupling like and different phosphorus-containing amides via one or more different coupling agents. In a particularly preferred embodiment, the mixture of Formula I compounds includes compounds wherein n' is 1 and $R^8$ is —ROH and coupled compounds wherein n' is 2 and $R^8$ is

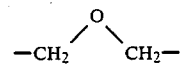

Phosphorus-containing amides will be disclosed and described first, followed by a disclosure and description of coupling agents which in turn will be followed by a description and disclosure of coupled amide compounds encompassed by generally Formula I.

PHOSPHORUS-CONTAINING AMIDES

The phosphorus-containing amides which are coupled to make compounds of Formula I can be made by various alternative routes. A preferred route involves the reaction of (A) an acid having the formula

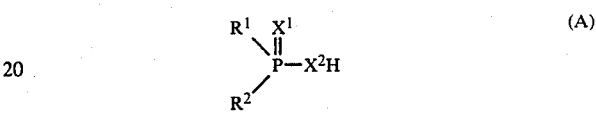

with (B) an acrylamide-type compound having the formula

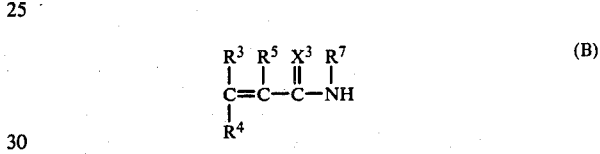

wherein the various R and the various X groups are as set forth above. That is, with regard to the acid, $X^1$ and $X^2$ are independently oxygen or sulfur with sulfur being preferred. $X^3$ is also oxygen, or sulfur, but oxygen is preferred. $R^1$ and $R^2$ are independently a hydrocarbyl, a hydrocarbyl-based oxy (preferably, the hydrocarbyl portion containing 6–22 carbons), or a hydrocarbyl-based thio with the hydrocarbyl-based oxy being preferred. Accordingly, the preferred type of (A) compound is a phosphorodithioic acid wherein the hydrocarbyl groups are both alkyl, both aromatic, or one of each as noted hereinabove. Similarly, $R^3$, $R^4$ and $R^5$ are the same as set forth above with hydrogen or methyl being preferred. $R^7$ can be an alkyl having from 1 to 22 carbon atoms with hydrogen being preferred. The phosphorodithioic acids (Formula A wherein $X^1$ and $X^2$ are sulfur) of the present invention can be made according to any conventional method as well known to the art. Generally, an alcohol, e.g., alkyl alcohol, aromatic alcohol, or both, is reacted with a phosphorus sulfide such as $P_2S_5$. A suitable reaction route is set forth in U.S. Pat. No. 3,361,668 hereby fully incorporated by reference for the purpose of disclosing such a reaction route. Examples of the (B) type reactant include acrylamide, methacrylamide wherein $R^5$ is methyl, and crotonamide. The phosphorus-containing amide compounds and coupled compounds of the present invention are oil-soluble compounds. The need for oil-solubility is related to the carbon chain length of $R^1$-$R^8$. For example, if $R^8$ is methylene, $R^1$ and $R^2$ would contain 6 to 22 carbon atoms to provide oil-solubility.

The reaction between the (A) acid and the (B) amide compound is exothermic and hence only slight heat need by applied thereto. The reaction conveniently can be carried out in an inert atmosphere such as nitrogen as from about 25° C. to about 100° C. with from about 70°

C. to about 90° C. being preferred. The reaction can be carried out in the presence or absence of a menstruum. Desirably, the reaction takes place in a solvent medium which typically is a hydrocarbon menstruum such as toluene, xylene, hexane, heptane, kerosene, fuel oil, an oil of a lubricating viscosity, and the like or a chlorohydrocarbon such as chloroform, carbon tetrachloride, and the like, or an alcohol such as methanol, ethanol, propanol, butanol, 2-ethylhexanol, and the like. The menstruum, in addition to acting as such, imparts favorable processing characteristics such as controlling the exothermic reaction as well as preventing unwanted side reactions. The reaction time, while dependent upon temperature, is usually as short as one or two hours or less.

The reaction of an acid according to Formula A with an acrylamide-type compound of Formula B yields a compound having the following formula

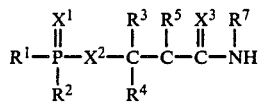

Formula of reaction product of (A) and (B).

At this point the $R^8$ of Formula I is hydrogen and n' is 1. This reaction product is an intermediate. However, it also can serve as an end product for use as an additive in a lubricating composition where it functions as a load-carrying agent, an extreme pressure anti-wear agent, a corrosion-inhibitor, and the like.

The intermediate reaction product of (A) and (B) can be coupled in a manner such as described below and/or further reacted in various ways known to those skilled in the art to include other functional groups $R^8$ on the nitrogen atom which groups include —ROH, —ROR, —RSR,

wherein R and R' are as defined above.

An alternative, although somewhat less desired, method of preparing phosphorus-containing amides relates to reacting an (A) acid having the formula

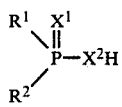 (A)

with (D) a compound having the formula

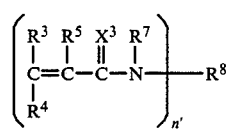 (D)

Dependent on what other substituents are, $R^1$ and $R^2$ may need to contain a larger number of carbon atoms in order to provide oil-solubility.

The (A) acid is the same as set forth above with regard to the preceding reaction product and hence $X^1$ and $X^2$ can be oxygen or sulfur with sulfur being preferred. While $X^3$ can also be oxygen or sulfur, oxygen is preferred. Similarly, $R^1$ and $R^2$ are the same as set forth above and hence will not be repeated. As previously noted, $R^1$ and $R^2$ can both be an alkyl having from 1 to 25, preferably 4 to 25 carbon atoms or can both be an alkyl-substituted aromatic wherein the alkyl substituent has from 1 to 28 carbon atoms. Moreover, one of the $R^1$ and $R^2$ groups can be an alkyl with the remaining group being an alkyl-substituted aromatic. Additionally, more than one acid having the above (A) formulation can be utilized having $R^1$ and $R^2$ substituents therein as set forth in the immediately preceding sentence thereby ensuring that a statistical mixture of the various alkyl and the various alkyl-substituted aromatic groups will exist.

Considering the (D) component, it is somewhat similar to compound Formula (B) set forth hereinabove except that it is coupled by an $R^8$ group. Accordingly, the definition of $R^3$, $R^4$, $R^5$ and $R^7$ is the same as set forth hereinabove with regard to compound (B) and hence will not be repeated but rather is fully hereby incorporated by reference. Thus, by way of summary, the various $R^3$, $R^4$, $R^5$ and $R^7$ groups are essentially saturated hydrocarbyls and preferably are either methyl or hydrogen. Considering $R^8$ is the same as discussed above with regard to Formula I. $R^8$ is preferably

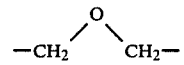

As with the reaction between acid (A) and compound (B), the reaction between acid (A) and compound (D) is also exothermic and thus requires only a slight amount of heat. Essentially the reaction of compound (D) with the (A) acid is very similar to the reaction of compound (B) and acid (A). Accordingly, the present reaction is carried out desirably in an inert atmosphere at a temperature from about 25° C. to about 100° C. with from about 70° C. to about 90° C. being preferred. The reaction time is generally short, for example on the order of less than an hour or two. Once again, hydrocarbon solvents such as toluene, xylene, hexane, heptane, kerosene, fuel oil, an oil of a lubricating viscosity, and the like or chlorinated hydrocarbon such as chloroform, carbon tetrachloride, and the like, or an alcohol such as methanol, ethanol, propanol, butanol, 2-ethylhexanol, and the like, are utilized. Once the product has been formed, the various solvents can be removed by stripping under a vacuum and the like.

Yet another alternative method of preparing compounds according to the present invention and especially the coupled compounds set forth hereinabove containing an $R^6$ group is via a displacement reaction. In this reaction, a metal salt of the (A) acid, that is a metal salt according to Formula E is reacted with a compound of Formula F

 (E)

is reacted with a compound of Formula F

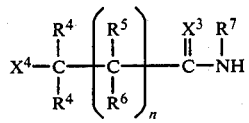

(F)

$X^1$, $X^2$, $X^3$, $R^1$, $R^2$, $R^3$, $R^4$, $R^5$, $R^6$, $R^7$ and n are the same as set forth above and accordingly the description thereof is hereby fully incorporated. M is an alkali metal such as sodium, potassium or the like, or an alkaline earth metal such as manganese, calcium or the like, or hydrogen, with sodium and potassium being preferred. Considering $X^4$, it is a displaceable halogen or carbon group well known to the art such as Cl Br, I, tosyl, mesyl, and the like. The reaction between the compounds of Formulae E and F proceeds in a manner very similar to that set forth above with regard to making the reaction product between compound A and compound B. Accordingly, the description with regard thereto will not be repeated. Briefly, the reaction is carried out at a temperature of about 10° C. to about 200° C. with from about 50° C. to about 150° C. being preferred. Naturally an inert atmosphere such as nitrogen is utilized. Although not required, the reaction can take place in a menstruum. The solvent also renders by-product salts, e.g., KCl, NaCl, NaBr, KBr, etc., which are insoluble in the reaction medium and easily removed by filtration. The amount of Formulae E and F compounds are generally an equivalent amount. The formed product has the following formula

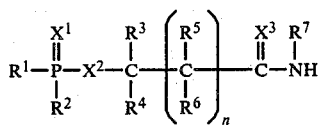

(II)

COUPLING AGENTS

After the reaction product of (A) and (B) is formed, these reaction products are preferably coupled by reacting them with a (C) aldehyde or ketone (or a reaction synthon equivalent of an aldehyde or ketone of the following formula

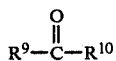

(C)

$R^9$ and $R^{10}$ independently can be hydrogen, an alkyl having from 1 to 12 carbon atoms, phenyl, or an alkyl-substituted phenyl having from 7 to 12 carbon atoms. Desirably compound (C) is an aldehyde, i.e., $R^{10}$ is H, having a total of 1 to 3 carbon atoms therein with one carbon atom, that is formaldehyde and paraformaldehyde being highly preferred which can result in methylene and di-methylene ether coupling groups.

The coupling reaction desirably takes place in the presence of strong mineral or organic acids such as HCl, $H_2SO_4$, $H_3PO_4$, $CH_3SO_3H$, p-toluenesulfonic acid, and the like. The amount of the acid catalyst is generally from about 0.3 to about 1.5% by weight, desirably from about 0.8 to about 1.2%, and preferably from about 0.9 to about 1.1% by weight based upon the weight of the total product formed. Although lesser amounts of catalyst can be utilized, the reaction is generally slower and a smaller fraction of the desired product is formed. The reaction with Formula C initially takes place at a temperature of from about 80° C. to about 120° C. and desirably from about 80° C. to about 100° C. in an inert atmosphere. The final reaction temperature is generally higher as from about 100° C. to about 150° C. and desirably from about 125° C. to about 135° C.

Alternatively, if one wishes to stop at the carbinol stage, (Formula II where X=O) the reaction between A and B is best carried out using basic catalysts, i.e., $NaHCO_3$, $KHCO_3$, $KHCO_3$, $Na_2CO_3$, $KCO_3$, NaOH, KOH, etc. This reaction mixture can be neutralized with acid and heated to remove water; reacted with $H_2S$, NaHS or $Na_2S$ or other source of $S^{-2}$; or, $NH_3$ or $R''NH_2$ where R'' is alternatively H, alkyl of 1–60 carbon atoms, aryl, alkyl substituents, aryl or aryl substituted alkyl of 6–30 carbon atoms or acyl of 1–22 carbon atoms to form the ether (Formula I, X=O), thio (Formula I, X=S) or amino (Formula I, X=N).

The amount of reactants (A) and (B) desirably is a 1:1 equivalent weight ratio although greater or lesser amounts can be utilized. A 1:1 equivalent weight ratio of the two reactants is desirable in that otherwise a higher acid number is obtained than desired or else one of the reactants is literally wasted. The amount of reaction product formed and reacted with coupling agent (C) is from about 0.3 to about 3.0 weight equivalents utilized per weight equivalent of said (C) aldehyde or ketone compound with a 1:1 equivalent ratio being preferred. The coupler (C) may be a mixture of different couplers and preferably includes paraformaldehyde.

The combination of formaldehyde and phosphorus containing amide compound as described above may couple two amides or may result in the formation of a —$CH_2OH$ on the nitrogen atom of the amide. Two of such amides with a —$CH_2OH$ group thereon may then be reacted to form a coupled amide with the coupling group being

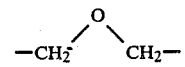

Such a coupling reaction may take place during use of such uncoupled compounds which reaction is endothermic. The endothermic reaction may be beneficial to the load-carrying lubricating properties of the overall oil composition.

Other couplers ($R^8$ in Formula I when n' is 2 or 3) and functional groups ($R^8$ in Formula I when n' is 1) can be attached to the nitrogen atoms of the phosphorus containing amides described above by procedures known to those skilled in the art.

As briefly discussed, above, the compounds of the present invention are particularly useful as additives for lubricating compositions. The compounds of the present invention are particularly useful as additives for lubrication where they function primarily as load-carrying agents, high or extreme pressure antiwear agents, oxidation inhibitors, corrosion-inhibitors, and the like. Lubricating compositions containing the compounds of the present invention as additives comprise a major proportion of a lubricating oil and a minor portion of said compound sufficient to improve the load-carrying ability, anti-wear ability, oxidation-inhibitor or corrosion-inhibiting properties of the composition. In general, the compounds are used in lubricants in an amount of from about 0.01 to about 5% by weight and desirably from about 0.1 to about 1% by weight based upon the total weight of the lubricating composition. Additionally, the compounds of the present invention can be utilized in a concentration from or a lubricant concentrate in an amount of from about 0.5 to about 50% by weight and more desirably from about 1 to about 25% by weight based upon the total weight of the concentrate package. In addition to the compounds of the present invention, the concentrate package can contain one or more compounds such as anti-wear agents, load-carrying agents, corrosion-inhibitors, oxidation inhibitors, demulsifiers, foam inhibitors, VI improvers, pour point depressants, detergents, dispersants, and the like. The compounds of the present invention can also be used as insecticides or pesticides.

COUPLED AMIDES

According to the present invention, various couplers are used to provide a variety of different types of coupled phosphorus-containing amides. Other reactions attach other functional groups to the phosphorus-containing amides. These uncoupled compounds may be present in a mixture with the paraformaldehyde coupled amides in a lubricant oil which is useful in providing the desirable properties or load-carrying agents, extreme pressure agents, and generally as additives in lubricating compositions.

A preferred form of the present invention is a statistical mixture of compounds having the following formula

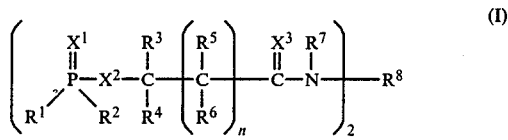

(I)

Considering $X^1$ $X^2$, it independently is oxygen or sulfur and preferably is sulfur whereas $X^3$ is O or S and preferably O. $R^1$ and $R^2$ each independently is a hydrocarbyl, a hydrocarbyl-based thio or preferably a hydrocarbyl-based oxy group wherein the hydrocarbyl portion contains 6 to 22 carbon atoms. The hydrocarbyl portion of $R^1$ and $R^2$ generally contains from 1 to about 34 carbon atoms. When $R^7$ is hydrogen and $R^8$ is methylene, $R^1$ and $R^2$ will contain 6 to 12 carbon atoms in order to provide for sufficient oil-solubility for the compound (I). The hydrocarbyl portion of $R^1$ and $R^2$ independently can be alkyl or aromatic. Although the hydrocarbyl portion of both $R^1$ and $R^2$ can be the same type of hydrocarbyl group, that is both alkyl or both aromatic, often one such group can be alkyl and the remaining group can be aromatic. Different Formula I compounds which are made by reacting a mixture of two or more different reactants each containing an alkyl hydrocarbyl group as well as an aromatic hydrocarbyl ($R^1$ and $R^2$) group therein. The same or different compounds are coupled via different coupling groups $R^8$ to form a statistical mixture of coupled compounds or are reacted with different compounds to provide different functional groups $R^8$ thereon.

The term "hydrocarbyl substituent" or "hydrocarbyl group" is meant throughout this entire specification as well as the claims herein to denote a group having a carbon atom directly attached to the remainder of the molecule and having predominantly hydrocarbon character within the context of this invention.

The hydrocarbyl group of $R^1$ or $R^2$ is preferably an alkyl containing from 6 to 22 (more preferably 8–12) carbon atoms. Examples of such groups include hexyl, heptyl, octyl, nonyl, decyl, dodecyl, tetradecyl, octadecyl, behenyl, and the like, including all isomers thereof. Should the $R^1$ or $R^2$ hydrocarbyl be an aromatic, it can be phenyl or naphthyl. Oftentime it will have an alkyl substituent thereon. Thus, the alkyl-substituted aromatic can have an alkyl substituent containing from 0, that is phenyl, to about 28 carbon atoms, and preferably from about 7 to about 12 carbon atoms. Whenever a blend of the compounds of Formula I is utilized containing significant or effective amounts of alkyl type $R^1$ or $R^2$ substituents, the aromatic substituent can contain preferably from about 6 to 12 carbon atoms in the alkyl group thereof, that is, the alkyl-substituted aromatic. This is because although the solubility of phenyl or low alkyl-substituted aromatics may be somewhat low, the overall solubility in a lubricant composition is generally increased to a desirable level through the utilization of the $R^1$ and $R^2$ hydrocarbyl portions which are alkyl and/or through the use of $R^7$ and/or $R^8$ groups which have a large number of carbon atoms therein. The use of lower alkyls, e.g., less than 6 carbon atoms at $R^1$ and $R^2$ above with a methylene at $R^8$ is undesirable with respect to oil solubility.

Considering now the alkyl-substituted aromatic group, the aromatic preferably is phenyl while the alkyl can be the same as set forth hereinabove. Specific examples of such alkyl groups on the aromatic nucleus include methyl, ethyl, propyl, butyl, pentyl, heptyl, octyl, decyl, behenyl, and the like including isomers thereof.

Accordingly, specific examples of mixed hydrocarbyl ($R^1$ and $R^2$) portions or substituents include tolyl and octyl, tolyl and hexyl, isobutylphenyl and amyl, phenyl and isooctyl, and the like. Mixed hydrocarbyl ($R^1$ and $R^2$) substituents are also assured when cresylic acids are utilized to form the phosphorus portion of the Formula I compound. The sources, type and variety of cresylic acids are known to those skilled in the art. The number of different molecular entities in the mixture is further increased by the different coupling groups, $R^8$ as defined above for Formula I when n' is 2 or 3.

When $X^1$ and $X^2$ is sulfur and especially when $X^2$ is sulfur, the alkyl hydrocarbyl substituent ($R^1$ or $R^2$) contains 6 or more carbon atoms. However, when $X^1$ or $X^2$ is oxygen and especially when $X^2$ is oxygen, the alkyl hydrocarbyl substituent ($R^1$ or $R^2$) is 6 to 12 carbon atoms.

Cosidering $R^3$, $R^4$, $R^5$ and $R^6$, each independently can be hydrogen or a saturated or unsaturated hydrocarbyl having up to 22 carbon atoms. The hydrocarbyl group can be an alkyl having from 1 to 22 carbon atoms, a cycloalkyl having from 4 to 22 carbon atoms, or an aromatic, an aromatic-substituted alkyl or an alkylsubstituted aromatic having from 6 to about 34 carbon atoms. Preferably, $R^3$, $R^4$, $R^5$ and $R^6$ is hydrogen or methyl with hydrogen being highly preferred. Examples of specific $R^3$, $R^4$, $R^5$ and $R^6$ alkyl groups include methyl, ethyl, propyl, butyl, pentyl, hexyl, heptyl, octyl, nonyl, decyl, dodecyl, tetradecyl, etc., as well as isomers thereof whereas examples of specific aromatic groups include phenyl, tolyl, naphthyl, heptylphenyl, nonylphenyl, dodecylphenyl, wax-substituted phenyl, and the like. With regard to the $R^5$—C—$R^6$ group, n can be 0 or 1. Preferably n is 1.

Considering now the amide portion of the molecule, $R^7$ is hydrogen or an alkyl having from 1 to 22 carbon atoms with hydrogen being highly preferred. Examples of specific alkyl groups include methyl, ethyl, propyl, butyl, and so forth including the various isomers thereof.

A particularly preferred embodiment of the invention includes a statistical mixture (i.e., coupled and uncoupled compounds each with different substituent groups providing a variety of different compounds) of different phosphorus containing amide compounds bonded to or coupled by different $R^8$ groups with the proviso that in general Formula I the mixture includes some compounds wherein n' is 1 and $R^8$ is —CH$_2$OH and also where n' is 2, $R^8$ is

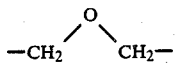

Any such statistical mixture is likely to include some coupled amide compounds of Formula I wherein $R^8$ is methylene. When $R^8$ is methylene, $R^1$ and $R^2$ generally must contain more than 6 carbon atoms in order to maintain good oil solubility. When n' is 1, $R^8$ is selected from the group consisting of H, —ROH, —ROR, —RSR and RN(R)$_2$ and when n' is 2 or 3, $R^8$ is selected from the group consisting of

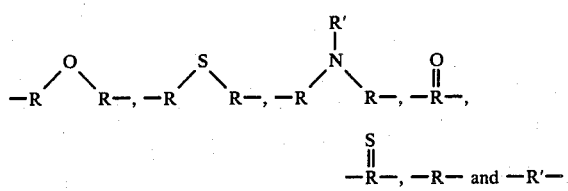

and when n' is 3, $R^8$ is

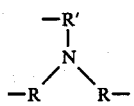

wherein R is independently hydrogen or an alkyl moiety, alkylene or alkylidene of 1 to 12 carbon atoms and R' is hydrogen or an alkyl or carboxy alkyl moiety, alkylene or alkylidene of containing 1 to 60 carbon atoms, R is preferably methylene and R' is preferably an alkyl moiety of 1 to 28 carbons. When R and R' are linking groups, they may be alkylene and/or alkylidene, i.e., the linkage may be vicinal and/or geminal. Compounds of Formula I are believed to be novel compounds and those which are oil-soluble are of particular interest to the present invention.

The following illustrate the preparation of compounds of the present invention. All parts and percentages are by weight unless otherwise indicated.

EXAMPLE 1

To a mixture of 1775 parts (4.26 equivalents) of O,O-di-isooctyl phosphorodithioic acid and 980 parts of toluene under a nitrogen atmosphere are added 302 parts (4.26 equivalents) of acrylamide. The reaction mixture exotherms to about 56° C. and 77 parts (2.33 equivalents) of paraformaldehyde and 215 parts (0.11 equivalent) of p-toluenesulfonic acid hydrate are added. Heating is continued at reflux (92°-127° C.) while removing 48 parts of water. Upon cooling the mixture to 100° C., 9.2 parts (0.11 equivalent) of sodium bicarbonate is added and cooling continued to about 30° C. A vacuum is applied (15 mm. Hg) and toluene solvent removed while raising the temperature of 110° C. The residue is filtered through a filter aid and the filtrate is the desired product. The product contains 6.86% P (6.74% theory).

EXAMPLE 2

To a mixture of 1494 parts (3.79 equivalents) of O,O-di-isooctyl phosphorodithioic acid and 800 parts of toluene under a nitrogen atmosphere are added 537 parts (3.79 equivalents) of 50% aqueous acrylamide solution over a period of one hour. The reaction mixture exotherms to about 53° C. and 64 parts (1.93 equivalents) of paraformaldehyde and 18 parts (0.095 equivalent) of p-toluenesulfonic acid hydrate are added. Heating is continued at reflux (91°-126° C.) for 4 hours while collecting 305 parts of water. The mixture is cooled to about 90° C. and 7.6 parts (0.095 equivalent) of 50% aqueous sodium hydroxide solution are added. Cooling is continued to about 30° C. and a vacuum is applied (15 mm. Hg). Toluene solvent is removed while raising the temperature to 110° C. The residue is filtered through a filter aid and the filtrate is the desired product. The product contains 6.90% P (6.75% theory) and 2.92% N (2.97% theory).

EXAMPLE 3

To a mixture of 984 parts (1.30 equivalents) of O,O-p-di-dodecylphenyl phosphorodithioic acid and 575 parts of toluene under a nitrogen atmosphere are added 100 parts (0.65 equivalent) of methylenebisacrylamide. The reaction mixture exotherms to about 40° C. and is heated at 80°-85° C. for 2 hours. After cooling the mixture to 30° C., a vacuum (15 mm. Hg) is applied and toluene solvent is removed while raising the temperature to 100° C. The residue is filtered through a filter aid and the filtrate is the desired product. The product contains 4.09% P (4.31% theory).

EXAMPLE 4

A reaction vessel is charged with 820 parts of toluene and 930 parts (2.32 equivalents) of a O,O-di-alkyl phosphorodithioic acid prepared from a mixture of 20 mole percent isobutyl alcohol and 80 mole percent 2-ethylhexyl alcohol. To this mixture under a nitrogen atmosphere are added 178.6 parts (1.16 equivalents) of methylenebisacrylamide. The mixture exotherms to about 65° C. and is heated at about 80°-85° C. for 2 hours. Upon cooling to 50° C., a vacuum (30 mm. Hg) is applied. Toluene solvent is removed while raising the temperature to 115° C. The residue is filtered through a filter aid and the filtrate is the desired product. The product contains 7.30% P (7.28% theory).

EXAMPLE 5

To a mixture of 305 parts of toluene and 611 parts (1.82 equivalents) of a O,O-di-alkyl-substituted phosphorodithioic acid prepared from a mixture of 20 mole percent phenol and 80 mole percent i-octyl alcohol, are added 258 parts (1.82 equivalents) of a 50% aqueous acrylamide solution over a 20-minute period under a nitrogen atmosphere. After an initial exotherm to 60° C., 32.1 parts (0.97 equivalent) of paraformaldehyde and 7.3 parts (0.038 equivalent) of p-toluenesulfonic acid hydrate are added. The mixture is heated at reflux (91°–127° C.) for 2 hours while removing 131 parts of water. The mixture is cooled to 80° C. and 3.1 parts (0.038 equivalent) of 50% aqueous sodium hydroxide solution is added. Cooling is continued to 50° C. and a vacuum (30 mm. Hg) is applied. Toluene solvent is removed while raising the temperature to 100° C. The residue is filtered through a filter aid and the filtrate is the desired product. The product contains 7.09% P (7.42% theory).

EXAMPLE 6

To 1017 parts (3.0 equivalents) of O,O-di-4-methyl-2-pentyl phosphorodithioic acid under nitrogen is added 213 parts (3.0 equivalents) of acrylamide. The reaction exotherms to 65° C. and held for one to three hours at 65°–75° C. The product is filtered through a filter aid and the filtrate is the desired product. The product contains 7.65% P (7.82% theory), 3.51% N (3.50% theory), and 16.05% S (16.06% theory).

EXAMPLE 7

To 614 parts (1.5 equivalents) of O,O-di-isooctyl phosphorodithioic acid under nitrogen is added 213 parts (1.5 equivalents) of a 50% aqueous acrylamide solution. The reaction exotherms to 65° and held for two hours at 70° C. A vacuum is applied (20 mm. Hg) while raising temperature to 90° C. The residue is filtered through a filter aid and the filtrate is the desired product. The product contains 6.67% P (6.60% theory), 2.94% N (2.97% theory), and 14.50% S (13.60% theory).

EXAMPLE 8

To 1340 parts (3.41 equivalents) of O,O-di-isooctyl phosphorodithioic acid under nitrogen is added 242 parts (3.41 equivalents) of acrylamide. The reaction exotherms to 60° C. and is held at 65°–70° C. for one hour. To this mixture are added 400 parts of toluene, 14 parts of potassium carbonate, and 307 parts (3.58 equivalents) of 35% aqueous formaldehyde. The mixture is heated under a nitrogen atmosphere at 35°–40° C. for 16 hours. To this mixture is added 18.2 parts of glacial acetic acid.

EXAMPLE 9

From the product of Example 8, water is removed using a Dean Stark trap at reflux for 6 hours. After 234 parts of water is collected (temperature is 120° C.), the mixture is cooled to 30° C. A vacuum is applied (30 mm. Hg) while raising temperature to 115° C. The mixture is filtered through a filter aid and the filtrate is the desired product. The product contains 6.71% phosphorus.

As previously noted, the compositions of the present invention are useful as additives for lubricants and functional fluids. They can be employed in a variety of lubricants based on diverse oils of lubricating viscosity, including natural and synthetic lubricating oils and mixtures thereof.

These lubricating compositions containing the subject additive concentrates are effective as crankcase lubricating oils for spark-ignited and compression-ignited internal combustion engines, including automobile and truck engines, two-cycle engines, aviation piston engines, marine, railroad and low-load diesel engines, and the like. Also, automatic transmission fluids, transaxle lubricants, gear lubricants, metal-working lubricants, hydraulic fluids, and other lubricating oil and grease compositions can benefit from the incorporation of the subject additive concentrates.

As noted above, the coupled phosphorus-containing amide type compounds of the present invention can be added directly to the lubricant in amounts as set forth above. Additionally, they are often diluted with a substantially inert, normally liquid organic diluent such as mineral oil, naphtha, benzene, toluene, xylene, and the like to form an additive concentrate. The concentrates can furthermore contain one or more additives known to the art or described hereinabove. The remainder of the concentrate is a substantially inert normally liquid diluent.

An example of a concentrate is as follows:
Product of Example 2: 15% by wt.
Zn salt of a phosphorodithioic acid: 50% by wt.
Oxidation inhibitor: 20% by wt.
Rust inhibitor: 5% by wt.
Mineral oil: 10% by wt.

The concentrate had good solubility with regard to the product of Example 2 therein.

When one part by weight of the above concentrate was used in 99 parts by weight of a mineral oil and the resulting solution tested with regard to a F.Z.G. gear test, an improvement from a pass 10 load stage to a pass 12 load stage was noted.

While in accordance with the patent statutes, a best mode and preferred embodiment has been set forth, it is to be understood that various modifications thereof will become apparent to those skilled in the art upon a reading of the specification. Therefore, it is to be understood that the invention disclosed herein is intended to cover such modifications as fall within the scope of the attached claims.

We claim:

1. A lubricating composition comprising a major portion of a lubricating oil and a minor portion of an oil soluble load carrying agent comprising:
the reaction product of an acid (A) having the formula:

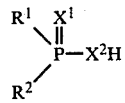

wherein $X^1$ and $X^2$, independently, is O or S;
wherein $R^1$ and $R^2$, independently, is a hydrocarbyl moiety a hydrocarbyl-based oxy moiety, or a hydrocarbyl-based thio moiety having from 4 to about 34 carbon atoms; and
(B) a compound having the formula:

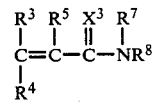

wherein $X^3$ is O or S; wherein $R^3$, $R^4$, and $R^5$, independently, is hydrogen or a saturated or unsaturated hydrocarbyl having from 1 to 34 carbon atoms, wherein $R^7$ is hydrogen or an alkyl having from 1 to 22 carbon atoms, wherein $R^8$ is selected from the group consisting of —H, —ROH, —ROR, —RSR, and

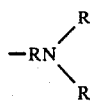

wherein each R is independently hydrogen or an alkyl moiety in the form of an alkylene or alkylidene containing 1 to 12 carbon atoms, and the subsequent reaction of the product formed thereby with (C) a compound having the formula:

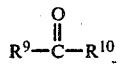

where $R^9$ and $R^{10}$, independently, is hydrogen, an alkyl moiety having from 1 to 12 carbon atoms, phenyl, or an alkyl substituted phenyl having from 7 to 12 carbon atoms.

2. A lubricating composition according to claim 1, where $R^9$ and $R^{10}$, independently, is hydrogen or an alkyl moiety having from 1 to 12 carbon atoms.

3. A lubricating composition according to claim 2, wherein $R^3$, $R^4$ and $R^5$, independently, is hydrogen, an alkyl moiety having from 1 to 22 carbon atoms, an aromatic or an alkyl-substituted aromatic having from 6 to 34 carbon atoms, and wherein said hydrocarbyl portion of $R^1$ and $R^2$, independently, is hydrogen an alkyl moiety having from 4 to about 25 carbon atoms or an aromatic, which may be substituted with an alkyl substituent containing 1 to about 28 carbon atoms.

4. A lubricating composition according to claim 3, wherein $X^1$ and $X^2$ is S, wherein $X^3$ is O, wherein $R^1$ and $R^2$ is a hydrocarbyl-based oxy wherein said hydrocarbyl portion is, independently, an alkyl moiety having from 6 to 12 carbon atoms or an aromatic moiety, which may be substituted with an alkyl substituent containing 1 to 12 carbon atoms, and wherein $R^9$ and $R^{10}$, independently, is hydrogen or an alkyl having 1 or 2 carbon atoms, and wherein $R^7$ is hydrogen.

5. A lubricating composition according to claim 4, wherein $R^3$, $R^4$ and $R^5$, independently, is hydrogen or methyl.

6. A lubricating composition according to claim 1, wherein $X^1$ and $X^2$ is S, wherein $X^3$ is O, wherein $R^1$ and $R^2$ is a hydrocarbyl-based oxy moiety wherein said hydrocarbyl portion is, independently, an alkyl moiety having from 6 to 12 carbon atoms or an alkyl-substituted aromatic wherein said alkyl substituent has from 7 to 12 carbon atoms; wherein $R^3$, $R^4$ and $R^5$, independently, is hydrogen or methyl, wherein R7 is hydrogen; and wherein $R^9$ and $R^{10}$ is hydrogen.

7. A lubricating composition comprising a major portion of a lubricating oil and a minor portion of an oil soluble load carrying agent having the formula:

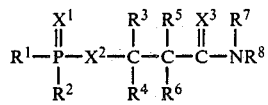

wherein $X^1$ and $X^2$ is S and $X^3$ is O;

wherein $R^1$ and $R^2$, independently is a hydrocarbyl moiety, a hydrocarbyl-based oxy moiety wherein the hydrocarbyl portion is independently an alkyl moiety having 6 to 22 carbons or an aromatic moiety which maybe substituent with an alkyl substituent having 1 to 12 carbons atoms, or a hydrocarbyl-based thio, having from 1 to about 34 carbon atoms;

wherein $R^3$, $R^4$, $R^5$, and $R^6$, independently, is hydrogen, or an alkyl moiety having from about 1 to 22 carbon atoms, a cycloalkyl moiety having from about 4 to 22 carbon atoms, or an aromatic moiety, an alkyl-substituted aromatic moiety or an aromatic-substituted alkyl moiety having from 6 to about 34 carbon atoms;

wherein $R^7$ is hydrogen or an alkyl having from 1 to 22 carbon atoms; and $R^8$ is selected from the group consisting of of —H, —ROH, —ROR, —RSR, and

wherein each R is independently hydrogen or an alkyl moiety in the form of an alkylene or alkylidene containing 1 to 12 carbon atoms.

8. A lubricating composition according to claim 7, wherein $R^3$, $R^4$, $R^5$ and $R^6$, independently, is hydrogen or methyl; wherein $R^7$ is hydrogen; and wherein $X^1$ and $X^2$ is S, and wherein $X^3$ is O.

9. A lubricating composition according to claim 8, wherein said alkyl portion of $R^1$ and $R^2$ is octyl.

* * * * *